United States Patent [19]

Balko et al.

[11] 4,289,766

[45] Sep. 15, 1981

[54] HETEROCYCLIC CARBOTHIOAMIDES

[75] Inventors: Terry W. Balko, Waldron; Ronald E. Hackler, Greenfield, both of Ind.

[73] Assignee: Eli Lilly and Company, Indianapolis, Ind.

[21] Appl. No.: 865,094

[22] Filed: Dec. 27, 1977

[51] Int. Cl.³ .................................................. C07D 277/04
[52] U.S. Cl. ............................... 424/246; 424/263; 424/267; 424/280; 548/200; 548/201; 548/209; 548/152; 544/55; 544/58.1; 544/58.7; 544/405
[58] Field of Search ............... 424/270, 246, 263, 267; 260/306.8 R; 548/152, 280, 200, 201; 546/209; 544/55, 58.1, 58.7, 405, 336

[56] References Cited

U.S. PATENT DOCUMENTS

| | | | |
|---|---|---|---|
| 3,821,239 | 6/1974 | Guillot et al. | 260/306.8 R |
| 3,853,865 | 12/1974 | Brenner et al. | 260/306.8 R |
| 4,011,230 | 3/1977 | Lies et al. | 260/306.7 R |
| 4,056,620 | 11/1977 | White | 260/306.7 R |

OTHER PUBLICATIONS

Stacey et al., J. Org. Chem. 23 1760 (1958).
Yamamoto et al., Chem. Abstr. 81 136039z (1974).
Klayman et al., J. Het. Chem. 5 517 (1968).

*Primary Examiner*—Nicholas S. Rizzo
*Attorney, Agent, or Firm*—Karen B. O'Connor; Arthur R. Whale; Leroy Whitaker

[57] ABSTRACT

2-Substituted-N-(3-substituted phenyl)thiazolidine-, tetrahydro-2H-1,3-thiazine-, and benzothiazoline-3-carbothioamides, useful as insecticides.

87 Claims, No Drawings

HETEROCYCLIC CARBOTHIOAMIDES

BACKGROUND OF THE INVENTION

This invention relates to heterocyclic carbothioamides. More particularly, this invention relates to 2-substituted-N-(3-substituted phenyl)thiazolidine-, tetrahydro-2H-1,3-thiazine-, and benzothiazoline-3-carbothioamides which are useful as insecticides.

Compounds containing the thiazolidine nucleus are not new; see, e.g., G. W. Stacy et al., *J. Org. Chem.*, 23, 1760 (1958). Most of the 2-substituted thiazolidines appear to be 2-iminothiazolidines. The non-imino compounds, on the other hand, are primarily 2-thioureido-2-thiazolines. See, for example, E. Cherbuliez et al., *Helv. Chim. Acta*, 49, 807 (1966) [*Chem. Abstr.*, 64, 158664d (1966)]; Y. Yamamoto et al., *Kyoritsu Yakka Daigaku Kerkyu Nempo*, 1973, 53 [*Chem. Abstr.*, 81, 136039z (1974)]; D. L. Klayman et al., *Tetrahedron Lett.*, 1967, 281 [*Chem. Abstr.*, 66., 94943x (1967)]; D. L. Klayman et al., *J. Heterocycl. Chem.*, 5, 517 (1968); S. P. Kharida et al., *J. Indian Chem. Soc.*, 37, 305 (1960) [*Chem. Abstr.*, 55, 10373a (1961)]; and D. L. Klayman et al., *Tetrahedron*, 25, 191 (1969). No utilities appear to have been disclosed for any of such compounds.

T. P. Forrest et al., *Can. J. Chem.*, 52, 2725 (1974), disclose 5-methoxy-2-phenylamino-2-thiazoline and 2-(1,3-diphenylthioureido)-5-methoxy-2-thiazoline. Again, no utilities are disclosed. Finally, R. E. Hackler et al., *Synthetic Communications*, 5, 143 (1975), disclose the formation of 2-substituted-2-thiazolines from haloalkyl isothiocyanates. Examples of such 2-substituents include dimethylamino, piperidino, and 4-methylpiperidino. No utilities were given.

SUMMARY OF THE INVENTION

In accordance with the present invention, heterocyclic carbothioamides are provided, having the formula,

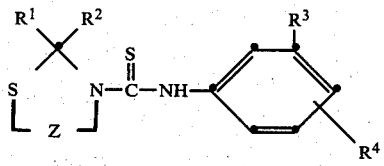

wherein
$R^1$ represents
(A) $C_1$-$C_{18}$ alkyl;
(B) $C_2$-$C_{18}$ alkenyl;
(C) $C_4$-$C_{18}$ alkadienyl;
(D) $C_3$-$C_{12}$ cycloalkyl, optionally substituted with either one or two $C_1$-$C_3$ alkyl groups;
(E) $C_5$-$C_{12}$ cycloalkenyl, optionally substituted with either one or two $C_1$-$C_3$ alkyl groups;
(F) $C_6$-$C_{12}$ cycloalkadienyl, optionally substituted with either one or two $C_1$-$C_3$ alkyl groups;
(G) phenyl, optionally substituted with from one to three groups selected from the group consisting of
(1) $C_1$-$C_6$ alkyl,
(2) $C_1$-$C_6$ alkoxy,
(3) $C_1$-$C_6$ alkylthio,
(4) trifluoromethyl,
(5) halo, and
(6) cyano;
(H) (cycloalkyl)alkyl, containing no more than about 18 carbon atoms, in which the cycloalkyl moiety is as defined hereinabove;
(I) phenylalkyl, containing no more than about 18 carbon atoms, in which the phenyl moiety is as defined hereinabove;
(J) diphenylalkyl, containing no more than about 18 carbon atoms, in which each phenyl moiety is as defined hereinabove;
(K) pyridyl, optionally substituted with either one or two groups selected from the group consisting of
(1) $C_1$-$C_3$ alkyl,
(2) $C_1$-$C_3$ alkoxy, or
(3) halo;
(L) piperidino attached at a position other than the nitrogen atom, optionally substituted with either one or two $C_1$-$C_3$ alkyl groups;
(M) morpholino attached at a position other than the nitrogen atom;
(N) pyrazinyl, optionally substituted with either one or two $C_1$-$C_3$ alkyl groups;
(O) pyridylalkyl, containing no more than about 17 carbon atoms, in which the pyridyl moiety is as defined hereinabove;
(P) piperidinoalkyl, containing no more than about 17 carbon atoms, in which the piperidino moiety is as defined hereinabove;
(Q) morpholinoalkyl, containing no more than about 16 carbon atoms;
(R) pyrazinylalkyl, containing no more than about 16 carbon atoms, in which the pyrazinyl moiety is as defined hereinabove; or
(S) tetrahydrofurylalkyl, containing no more than about 17 carbon atoms;
$R^2$ represents hydrogen or $C_1$-$C_3$ alkyl;
$R^3$ represents
(A) halo,
(B) trifluoromethyl,
(C) cyano, or
(D) 1,1,2,2-tetrafluoroethoxy;
$R^4$ represents
(A) hydrogen,
(B) halo, or
(C) $C_1$-$C_3$ alkyl, with the provisos that when $R^4$ is halo it can not be in the 2-position and when $R^4$ is $C_1$-$C_3$ alkyl it can not be in the 4-position;
Z represents

in which each of $R^7$-$R^{16}$, inclusive, independently is hydrogen or $C_1$-$C_3$ alkyl, with the proviso that the two groups attached to any given carbon atom in (A) or (B) together can not contain more than four carbon atoms; and $R^{17}$ represents
(1) $C_1$–$C_3$ alkyl,
(2) $C_1$–$C_3$ alkoxy,
(3) $C_1$–$C_3$ alkylthio,
(4) trifluoromethyl,
(5) halo,
(6) cyano, or
(7) hydrogen;
with the proviso that when
Z represents

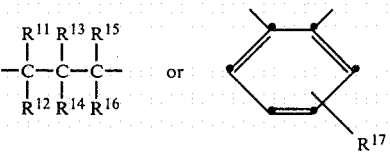

$R^2$ is hydrogen.

A preferred group of compounds comprises the compounds of the above formula wherein
$R^1$ represents
(1) alkyl,
(2) phenyl, optionally monosubstituted with halo or $C_1$–$C_3$ alkyl, or
(3) phenylalkyl, in which the phenyl moiety is unsubstituted;
$R^3$ is halo or trifluoromethyl;
$R^4$ is hydrogen; and
each of $R^7$–$R^{17}$, inclusive, is hydrogen.

Included within the above preferred group of compounds are the following more preferred embodiments:
(1) Z represents

$R^1$ represents alkyl, benzyl, or phenyl which is optionally monosubstituted with bromo;
$R^3$ is chloro or bromo; and
$R^4$ is hydrogen;
(2) Z represents

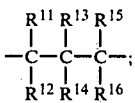

$R^1$ is alkyl or phenyl which is optionally monosubstituted with methyl, bromo, or chloro;
$R^2$ is hydrogen;
$R^3$ is bromo, chloro, or trifluoromethyl; and
$R^4$ is hydrogen;
(3) Z represents

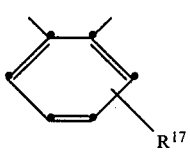

$R^1$ is $C_1$–$C_3$ alkyl;
$R^2$ is hydrogen;

$R^3$ is bromo or chloro; and
$R^4$ is hydrogen.

The present invention also provides a method for reducing or eradicating a population of the insect species *Epilachna varivestis* which comprises administering to the insect by ingestion an insecticidally-effective amount of a compound of Formula I.

Additionally, the present invention provides an insecticidal composition which comprises an insecticidally-effective amount of a compound of Formula I and an agriculturally-acceptable carrier.

DETAILED DESCRIPTION OF THE INVENTION

In the above formula, the various chemical groups have their usual meanings. For the sake of clarity, however, examples of the various generally-named groups will be given.

The term "$C_1$–$C_{18}$ alkyl" includes, among others, methyl, ethyl, propyl, isopropyl, butyl, isobutyl, pentyl, neopentyl, 1-methylbutyl, hexyl, isohexyl, 2,3-dimethylbutyl, 1-ethylpentyl, 2-ethyl-3-methylbutyl, 2-ethylhexyl, 6-methylheptyl, nonyl, 2,4,4-trimethylhexyl, decyl, 7,7-dimethyloctyl, 1-propylheptyl, 1,1-dimethyloctyl, undecyl, 3-ethyl-2,6-dimethylheptyl, 10-methylundecyl, 5-ethyl-2,6-dimethyloctyl, tridecyl, 2,2,6,6,7-pentamethyloctyl, 9-ethyldodecyl, pentadecyl, 5-sec-butyl-2,7-dimethylnonyl, 14-methylpentadecyl, 3-propyl-8-ethyldodecyl, octadecyl, 1-methylheptadecyl, and the like.

The terms "$C_2$–$C_{18}$ alkenyl" and "$C_4$–$C_{18}$ alkadienyl" include, among others, vinyl, 1-propenyl, allyl, isopropenyl, 1-butenyl, 2-butenyl, 1-pentenyl, 2-pentenyl, 2-methyl-2-butenyl, 1-hexenyl, 2-hexenyl, 3-hexenyl, 4-methyl-1-pentenyl, 2-methyl-1-pentenyl, 2-methyl-2-pentenyl, 3-methyl-2-pentenyl, 2,3-dimethyl-2-butenyl, 3,3-dimethyl-1-butenyl, 1-heptenyl, 2-heptenyl, 4-methyl-1-hexenyl, 2,4-dimethyl-1-pentenyl, 2-propyl-1-butenyl, 2,3,3-trimethyl-1-butenyl, 1-octenyl, 2-octenyl, 4-octenyl, 2,4,4-trimethyl-1-pentenyl, 1-nonenyl, 2,3-diethyl-2-pentenyl, 1-decenyl, 5-decenyl, 3-isopropyl-3-heptenyl, 4-undecenyl, 1-dodecenyl, 2-methyl-1-undecenyl, 2,2,4,6,6-pentamethyl-3-heptenyl, 1-tridecenyl, 3-tetradecenyl, 5-pentadecenyl, 1-hexadecenyl, 1,5-dimethyl-2-ethyl-3-propyl-4-nonenyl, 1-octadecenyl, 1,3-butadienyl, 1,3-pentadienyl, 1,4-pentadienyl, 2-methyl-1,3-butadienyl, 3-methyl-1,2-butadienyl, 1,2-hexadienyl, 1,4-hexadienyl, 1,5-hexadienyl, 2,4-hexadienyl, 2-ethyl-1,3-butadienyl, 2-methyl-1,3-pentadienyl, 4-methyl-1,3-pentadienyl, 2,3-dimethyl-1,3-butadienyl, 1,4-heptadienyl, 1,6-heptadienyl, 2,4-dimethyl-1,3-pentadienyl, 1,7-octadienyl, 2,5-dimethyl-2,4-hexadienyl, 1,8-nonadienyl, 7-methyl-2,4-octadienyl, 1,3-decadienyl, 2,6-dimethyl-2,6-octadienyl, 1,10-undecadienyl, 5,6-dimethyl-4-ethyl-1,2-heptadienyl, 1,5-dodecadienyl, 1,12-tridecadienyl, 4-isopropyl-1,9-decadienyl, 6,8-tetradecadienyl, 6,9-pentadecadienyl, 1,15-hexadecadienyl, 6,10-hexadecadienyl, 2,3,11-trimethyl-6,9-tridecadienyl, 7,10-heptadecadienyl, 1,17-octadecadienyl, 2-methyl-7,10-heptadecadienyl, and the like.

The term "$C_1$–$C_3$ alkyl" includes methyl, ethyl, propyl, and isopropyl. Thus, the phrase "$C_3$–$C_{12}$ cycloalkyl, optionally substituted with either one or two $C_1$–$C_3$ alkyl groups" is meant to include, among others, such groups as cyclopropyl, 2-ethylcyclopropyl, cyclobutyl, 2,3-dimethylcyclobutyl, cyclopentyl, 3-propylcyclopentyl, cyclohexyl, 2-methyl-4-isopropylcyclohexyl, cycloheptyl, 3-ethylcycloheptyl, cyclooctyl, cyclononyl, 3,5-diisopropylcyclononyl, cyclodecyl, 1-methyl-4-ethylcyclodecyl, cycloundecyl, cyclododecyl, and the like.

The phrases "$C_5$–$C_{12}$ cycloalkenyl, optionally substituted . . ." and "$C_6$–$C_{12}$ cycloalkadienyl, optionally substituted . . ." are meant to include, among others, such groups as cyclopentenyl, 2-ethylcyclopentenyl, cyclohexenyl, 4-methylcyclohexenyl, 2-isopropyl-5-methylcyclohexenyl, cycloheptenyl, cyclooctenyl, 3,5-dimethylcyclooctenyl, cyclononenyl, 2-ethylcyclononenyl, cyclodecenyl, 4-isopropyl-7-methylcyclodecenyl, cycloundecenyl, 5-methylcycloundecenyl, cyclododecenyl, 3-propylcyclododecenyl, 1,3-cyclohexadienyl, 5-methyl-1,3-cyclohexadienyl, 1,4-cyclohexadienyl, 1,3-cycloheptadienyl, 2,4-dimethyl-1,3-cycloheptadienyl, 2,4-cycloheptadienyl, 1,3-cyclooctadienyl, 1,4-cyclooctadienyl, 1,5-cyclooctadienyl, 1-methyl-2,5-cyclooctadienyl, 1,4-cyclononadienyl, 3,6-dipropyl-1,3-cyclononadienyl, 1,3-cyclodecadienyl, 3-ethyl-1,5-cyclodecadienyl, 2,6-cycloundecadienyl, 4-ethyl-5-methyl-1,7-cycloundecadienyl, 1,3-cyclododecadienyl, 1,7-cyclodecadienyl, 3-propyl-2,5-cyclododecadienyl, and the like.

The term "$C_1$–$C_6$ alkyl" and the alkyl moiety in the terms "$C_1$–$C_6$ alkylthio" and "$C_1$–$C_6$ alkoxy" include methyl, ethyl, propyl, isopropyl, butyl, isobutyl, sec-butyl, t-butyl, pentyl, isopentyl, 1-methylbutyl, 1-ethylpropyl, neopentyl, hexyl, isohexyl, and the like. Similarly, the phrase "phenyl, optionally substituted with . . ." is meant to include, among others, such groups as phenyl, m-tolyl, o-cumenyl, 4-hexylphenyl, 3-trifluoromethylphenyl, 3-isobutylthiophenyl, 2-ethoxyphenyl, 2-fluorophenyl, 3-chlorophenyl, 4-bromophenyl, 3-iodophenyl, 4-cyanophenyl, 2,6-xylyl, 2,4-bis(trifluoromethyl)phenyl, 2-methylthio-4-butylthiophenyl, 2,3-dimethoxyphenyl, 3,5-dichlorophenyl, 2-bromo-5-chlorophenyl, 3,4-dicyanophenyl, 3-trifluoromethyl-5-neopentylphenyl, 5-fluoro-2-methoxyphenyl, mesityl, 4-bromo-3,5-dimethylphenyl, 2-methyl-4-cyano-5-pentylphenyl, 2,5-dichloro-4-fluorophenyl, 2,4,6-triethoxyphenyl, and the like.

The phrase "(cycloalkyl)alkyl, containing . . ." includes, among others, cyclopropylmethyl, 6-(2-ethylcyclopropyl)hexyl, 2,3-dimethylcyclobutylmethyl, 7-cyclopentyl-2,2-dimethyloctyl, cyclohexylmethyl, 3-(3-isopropylcyclohexyl)propyl, 2-(1-methyl-4-ethylcyclooctyl)ethyl, 4-cycloundecylpentyl, and the like.

The phrases "phenylalkyl, containing . . ." and "diphenylalkyl, containing . . ." include, among others, benzyl, phenethyl, 4-(o-cumenyl)octyl, 3-(2-methyl-4-isohexyloxyphenyl)butyl, 1,3-dimethyl-6-(2-cyano-3-ethyl-5-fluorophenyl)heptyl, diphenylmethyl, 2-methyl-2-(m-tolyl)-3-(2,4-dichlorophenyl)propyl, and the like.

The phrase "pyridyl, optionally substituted . . ." includes, among others, 2-pyridyl, 3-pyridyl, 2-methyl-4-pyridyl, 5-ethoxy-3-pyridyl, 2,6-dichloro-4-pyridyl, 2-ethyl-5-methyl-3-pyridyl, and the like.

The phrases "piperidino . . . optionally substituted . . ." and "pyrazinyl, optionally substituted . . ." include, among others, 3-piperidino, 2,5-dimethyl-4-piperidino, 4-isopropyl-2-piperidino, 2-pyrazinyl, 5-ethyl-2-pyrazinyl, 3,5-dimethyl-2-pyrazinyl, and the like The phrases "pyridylalkyl, containing . . .", "piperidinoalkyl, containing . . .", "morpholinoalkyl, containing . . .", "pyrazinylalkyl, containing . . ." and "tetrahydrofurylalkyl, containing . . ." include, among others, 2-pyridylmethyl, 4-(4-pyridyl)heptyl, 2,2-dimethyl-3-(3,5-dimethoxy-2-pyridyl)propyl, 11-(2-piperidino)undecyl, 4-ethyl-4-(2-ethyl-4-piperidino)butyl, 1,1-dimethyl-2-(morpholino)ethyl, 1-ethyl-3-(3,6-dimethyl-2-pyrazinyl)propyl, (5-propyl-2-pyrazinyl)methyl, 4-tetrahydrofurylbutyl, 2-ethyl-5-tetrahydrofurylpentyl, and the like.

It will be understood that the present invention is not to be limited by the definitions and exemplification given herein. Various classes of compounds are contemplated, and such various classes of compounds can be employed in either the method or the insecticidal composition of the present invention. Examples of such contemplated various classes are given below. Each numbered subparagraph describes an independent class of compounds; in each class, the variables have the general meanings already given if not otherwise stated.

Compounds wherein:
1. $R^1$ represents alkyl;
2. $R^1$ represents alkenyl;
3. $R^1$ represents alkadienyl;
4. $R^1$ represents cycloalkyl or substituted cycloalkyl;
5. $R^1$ represents cycloalkenyl or substituted cycloalkenyl;
6. $R^1$ represents cycloalkadienyl or substituted cycloalkadienyl;
7. $R^1$ represents phenyl or substituted phenyl;
8. $R^1$ represents (cycloalkyl)alkyl or (subsituted cycloalkyl)alkyl;
9. $R^1$ represents phenylalkyl or (substituted phenyl)alkyl;
10. $R^1$ represents diphenylalkyl, phenyl(substituted phenyl)alkyl, or di(substituted phenyl)alkyl;
11. $R^1$ represents pyridyl, substituted pyridyl, piperidino, substituted piperidino, morpholino, pyrazinyl, or substituted pyrazinyl;
12. $R^1$ represents pyridylalkyl, (substituted pyridyl)alkyl, piperidinoalkyl, (substituted piperidino)alkyl, morpholinoalkyl, pyrazinylalkyl, (substituted pyrazinyl)alkyl, or tetrahydrofurylalkyl;
13. $R^1$ represents alkyl; phenyl, optionally monosubstituted with halo or $C_1$–$C_3$ alkyl; or phenylalkyl in which the phenol moiety is unsubstituted;
14. $R^1$ represents alkyl; benzyl; or phenyl, optionally monosubstituted with bromo;
15. $R^1$ represents alkyl; or phenyl, optionally monosubstituted with methyl, bromo, or chloro;
16. $R^1$ represents $C_1$–$C_3$ alkyl;
17. $R^1$ represents methyl, ethyl, propyl, isopropyl, or decyl;
18. $R^1$ represents phenyl;
19. $R^1$ represents o-tolyl;
20. $R^1$ represents 4-bromophenyl or 3-chlorophenyl;
21. $R^1$ represents benzyl;
22. $R^2$ represents hydrogen or $C_1$–$C_3$ alkyl;
23. $R^2$ represents hydrogen;
24. $R^2$ represents methyl;
25. $R^2$ represents ethyl;
26. $R^2$ represents propyl;
27. $R^3$ represents halo, trifluoromethyl, cyano, or 1,1,2,2-tetrafluoroethoxy;
28. $R^3$ represents halo or trifluoromethyl;
29. $R^3$ represents bromo or chloro;
30. $R^3$ represents bromo, chloro, or trifluoromethyl;
31. $R^4$ represents hydrogen, halo, or $C_1$–$C_3$ alkyl;
32. $R^4$ represents hydrogen;
33. Z represents

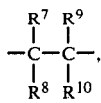

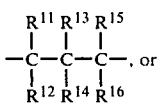

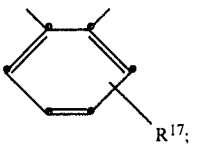

34. Z represents

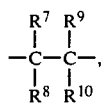

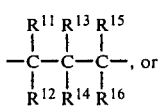

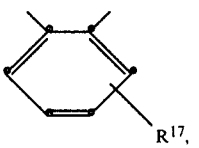

in which each of $R^7$–$R^{17}$, inclusive, represents hydrogen.

35. Z represents

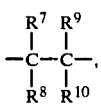

in which each of $R^7$–$R^{10}$, inclusive, represents hydrogen;

36. Z represents

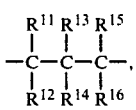

in which each of $R^{11}$–$R^{16}$, inclusive, represents hydrogen;

37. Z represents

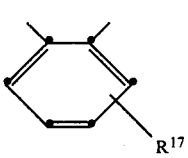

in which $R^{17}$ represents hydrogen;

38. The variables are as described in subparagraphs 13 and 25;
39. The variables are as described in subparagraphs 13 and 26;
40. The variables are as described in subparagraphs 13 and 28;
41. The variables are as described in subparagraphs 13 and 29;
42. The variables are as described in subparagraphs 13 and 30;
43. The variables are as described in subparagraphs 13 and 32;
44. The variables are as described in subparagraphs 13 and 34;
45. The variables are as described in subparagraphs 13 and 35;
46. The variables are as described in subparagraphs 13 and 36;
47. The variables are as described in subparagraphs 13 and 37;
48. The variables are as described in subparagraphs 14 and 23;
49. The variables are as described in subparagraphs 14 and 24;
50. The variables are as described in subparagraphs 14 and 25;
51. The variables are as described in subparagraphs 14 and 26;
52. The variables are as described in subparagraphs 14 and 29;
53. The variables are as described in subparagraphs 14 and 32;
54. The variables are as described in subparagraphs 14 and 35;
55. The variables are as described in subparagraphs 15 and 23;
56. The variables are as described in subparagraphs 15 and 24;
57. The variables are as described in subparagraphs 15 and 25;
58. The variables are as described in subparagraphs 15 and 26;
59. The variables are as described in subparagraphs 15 and 30;
60. The variables are as described in subparagraphs 15 and 32;
61. The variables are as described in subparagraphs 15 and 36;
62. The variables are as described in subparagraphs 16 and 23;
63. The variables are as described in subparagraphs 16 and 29;
64. The variables are as described in subparagraphs 16 and 32;
65. The variables are as described in subparagraphs 16 and 37;
66. The variables are as described in subparagraphs 13, 23, and 28;
67. The variables are as described in subparagraphs 13, 23, and 29;
68. The variables are as described in subparagraphs 13, 23, and 30;
69. The variables are as described in subparagraphs 13, 23, and 32;
70. The variables are as described in subparagraphs 13, 23, and 34;
71. The variables are as described in subparagraphs 13, 23, and 35;
72. The variables are as described in subparagraphs 13, 23, and 36;
73. The variables are as described in subparagraphs 13, 23, and 37;

74. The variables are as described in subparagraphs 13, 24, and 28;
75. The variables are as described in subparagraphs 13, 24, and 29;
76. The variables are as described in subparagraphs 13, 24, and 30;
77. The variables are as described in subparagraphs 13, 24, and 32;
78. The variables are as described in subparagraphs 13, 24, and 34;
79. The variables are as described in subparagraphs 13, 24, and 35;
80. The variables are as described in subparagraphs 13, 25, and 29;
81. The variables are as described in subparagraphs 13, 25, and 30;
82. The variables are as described in subparagraphs 13, 25, and 32;
83. The variables are as described in subparagraphs 13, 25, and 34;
84. The variables are as described in subparagraphs 13, 26, and 28;
85. The variables are as described in subparagraphs 13, 26, and 29;
86. The variables are as described in subparagraphs 13, 26, and 30;
87. The variables are as described in subparagraphs 13, 26, and 32;
88. The variables are as described in subparagraphs 13, 26, and 34;
89. The variables are as described in subparagraphs 13, 26, and 35;
90. The variables are as described in subparagraphs 14, 23, and 29;
91. The variables are as described in subparagraphs 14, 23, and 32;
92. The variables are as described in subparagraphs 14, 23, and 35;
93. The variables are as described in subparagraphs 14, 24, and 29;
94. The variables are as described in subparagraphs 14, 24, and 32;
95. The variables are as described in subparagraphs 14, 24, and 35;
96. The variables are as described in subparagraphs 14, 25, and 29;
97. The variables are as described in subparagraphs 14, 25, and 32;
98. The variables are as described in subparagraphs 14, 25, and 35;
99. The variables are as described in subparagraphs 14, 26, and 29;
100. The variables are as described in subparagraphs 14, 26, and 32;
101. The variables are as described in subparagraphs 14, 26, and 35;
102. The variables are as described in subparagraphs 15, 23, and 30;
103. The variables are as described in subparagraphs 15, 23, and 32;
104. The variables are as described in subparagraphs 15, 23, and 36;
105. The variables are as described in subparagraphs 15, 24, and 30;
106. The variables are as described in subparagraphs 15, 24, and 32;
107. The variables are as described in subparagraphs 15, 25, and 30;
108. The variables are as described in subparagraphs 15, 25, and 32;
109. The variables are as described in subparagraphs 15, 26, and 30;
110. The variables are as described in subparagraphs 15, 26, and 32;
111. The variables are as described in subparagraphs 16, 23, and 29;
112. The variables are as described in subparagraphs 16, 23, and 32;
113. The variables are as described in subparagraphs 16, 23, and 37;
114. The variables are as described in subparagraphs 13, 23, 28, and 30;
115. The variables are as described in subparagraphs 13, 23, 28, and 32;
116. The variables are as described in subparagraphs 13, 23, 28, and 36;
117. The variables are as described in subparagraphs 13, 23, 28, and 37;
118. The variables are as described in subparagraphs 13, 24, 28, and 32;
119. The variables are as described in subparagraphs 13, 24, 28, and 35;
120. The variables are as described in subparagraphs 13, 24, 28, and 36;
121. The variables are as described in subparagraphs 13, 24, 28, and 37;
122. The variables are as described in subparagraphs 13, 25, 28, and 32;
123. The variables are as described in subparagraphs 13, 25, 28, and 35;
124. The variables are as described in subparagraphs 13, 26, 28, and 32;
125. The variables are as described in subparagraphs 13, 26, 28, and 35;
126. The variables are as described in subparagraphs 13, 23, 29, and 32;
127. The variables are as described in subparagraphs 13, 23, 29, and 35;
128. The variables are as described in subparagraphs 13, 23, 29, and 36;
129. The variables are as described in subparagraphs 13, 23, 29, and 37;
130. The variables are as described in subparagraphs 13, 24, 29, and 32;
131. The variables are as described in subparagraphs 13, 24, 29, and 35;
132. The variables are as described in subparagraphs 13, 25, 29, and 32;
133. The variables are as described in subparagraphs 13, 25, 29, and 35;
134. The variables are as described in subparagraphs 13, 26, 29, and 32;
135. The variables are as described in subparagraphs 13, 26, 29, and 35;
136. The variables are as described in subparagraphs 13, 23, 30, and 32;
137. The variables are as described in subparagraphs 13, 23, 30, and 35;
138. The variables are as described in subparagraphs 13, 23, 30, and 36;
139. The variables are as described in subparagraphs 13, 23, 30, and 37;
140. The variables are as described in subparagraphs 13, 24, 30, and 32;
141. The variables are as described in subparagraphs 13, 24, 30, and 35;

142. The variables are as described in subparagraphs 13, 25, 30, and 32;
143. The variables are as described in subparagraphs 13, 25, 30, and 35;
144. The variables are as described in subparagraphs 13, 26, 30, and 32;
145. The variables are as described in subparagraphs 13, 26, 30, and 35;
146. The variables are as described in subparagraphs 14, 23, 29, and 32;
147. The variables are as described in subparagraphs 14, 23, 29, and 35;
148. The variables are as described in subparagraphs 14, 24, 29, and 32;
149. The variables are as described in subparagraphs 14, 24, 29, and 35;
150. The variables are as described in subparagraphs 14, 25, 29, and 32;
151. The variables are as described in subparagraphs 14, 25, 29, and 35;
152. The variables are as described in subparagraphs 14, 26, 29, and 32;
153. The variables are as described in subparagraphs 14, 26, 29, and 35;
154. The variables are as described in subparagraphs 13, 23, 29, 32, and 35;
155. The variables are as described in subparagraphs 13, 23, 28, 32, and 36;
156. The variables are as described in subparagraphs 13, 23, 28, 32, and 37;
157. The variables are as described in subparagraphs 13, 23, 28, 32, and 35;
158. The variables are as described in subparagraphs 13, 25, 28, 32, and 35;
159. The variables are as described in subparagraphs 13, 26, 28, 32, and 35;
160. The variables are as described in subparagraphs 13, 23, 29, 32, and 35;
161. The variables are as described in subparagraphs 13, 23, 29, 32, and 36;
162. The variables are as described in subparagraphs 13, 23, 29, 32, and 37;
163. The variables are as described in subparagraphs 13, 24, 29, 32, and 35;
164. The variables are as described in subparagraphs 13, 25, 29, 32, and 35;
165. The variables are as described in subparagraphs 13, 26, 29, 32, and 35;
166. The variables are as described in subparagraphs 14, 23, 29, 32, and 35;
167. The variables are as described in subparagraphs 14, 24, 29, 32, and 35;
168. The variables are as described in subparagraphs 14, 25, 29, 32, and 35;
169. The variables are as described in subparagraphs 14, 26, 29, 32, and 35;
170. The variables are as described in subparagraphs 15, 23, 30, 32, and 36;
171. The variables are as described in subparagraphs 16, 23, 29, 32, and 37;
172. The variables are as described in subparagraphs 17, 23, 28, 32, and 35;
173. The variables are as described in subparagraphs 17, 23, 29, 32, and 35;
174. The variables are as described in subparagraphs 17, 23, 29, 32, and 37;
175. The variables are as described in subparagraphs 17, 26, 29, 32, and 35;
176. The variables are as described in subparagraphs 18, 23, 29, 32, and 35;
177. The variables are as described in subparagraphs 18, 23, 30, 32, and 36;
178. The variables are as described in subparagraphs 18, 24, 28, 32, and 35;
179. The variables are as described in subparagraphs 18, 24, 29, 32, and 35;
180. The variables are as described in subparagraphs 18, 25, 29, 32, and 35;
181. The variables are as described in subparagraphs 19, 23, 29, 32, and 35;
182. The variables are as described in subparagraphs 20, 23, 29, 32, and 35;
183. The variables are as described in subparagraphs 20, 23, 30, 32, and 36;
184. The variables are as described in subparagraphs 21, 23, 29, 32, and 35; and
185. The variables are as described in subparagraphs 21, 23, 29, 32, and 37.

It should be apparent from the foregoing that any and all possible combinations of variables are within the scope of the present invention. From the above examples of contemplated classes, it is possible for one having ordinary skill in the art to construct any desired class, whether specifically exemplified or not. Thus, the present invention consists of multiple subgenera, with each subgenus consisting of a contemplated class of compounds as illustrated above without being limited thereto. Stated differently, any subgenus not specifically set forth herein is still implicitly within the scope of the present invention.

In order to further clarify the present invention, the following list of compounds is given by way of illustration. It is to be understood, however, that the present invention is neither confined to nor limited by the compounds listed.

1. 2-t-butyl-5-isopropyl-N-(2-methyl-3-iodophenyl)-3-thiazolidinecarbothioamide,
2. 2-(2-ethylhexyl)-N-(3-fluorophenyl)-3-thiazolidinecarbothioamide,
3. N-(3-bromophenyl)-2-(3-isopropyl-1-methylundecyl)-2,4,5-triethyl-3-thiazolidinecarbothioamide,
4. 2-octadecyl-N-[3-(1,1,2,2-tetrafluoroethoxy)-phenyl]-3-thiazolidinecarbothioamide,
5. 2-cyclopropyl-N-(3,5-dibromophenyl)-5-isopropyl-5-methyl-2-propyl-3-thiazolidinecarbothioamide,
6. N-(3-chlorophenyl)-2-cyclopentyl-4-ethyl-4-methyl-3-thiazolidinecarbothioamide,
7. N-(3-cyanophenyl)-2-(4-methylcyclononyl)-3-thiazolidinecarbothioamide,
8. N-(2-chloro-3-trifluoromethylphenyl)-2-(4-ethoxyphenyl)-4-methyl-3-thiazolidinecarbothioamide,
9. N-(3-iodophenyl)-2-(4-iodophenyl)-3-thiazolidinecarbothioamide,
10. N-(3-chloro-2-ethylphenyl)-2,5-dimethyl-2-(4-trifluoromethylphenyl)-3-thiazolidinecarbothioamide,
11. 2-(5-bromo-2,4-dimethylphenyl)-N-(3-chloro-5-fluorophenyl)-5-propyl-3-thiazolidinecarbothioamide,
12. N-(3-chlorophenyl)-2-(5-cyclopropyl-3-ethylhexyl)-3-thiazolidinecarbothioamide,
13. 2-isopropyl-2-(2-methyl-2-phenylpropyl)-5-ethyl-N-(3-trifluoromethylphenyl)-3-thiazolidinecarbothioamide, 14. 2-[2-(2,4-dimethoxy-5-cyanophenyl)ethyl]-4,5-dimethyl-N-(3-fluorophenyl)-3-thiazolidinecarbothioamide,
15. 2-(2,4-diphenylbutyl)-N-(3-iodophenyl)-4-propyl-3-thiazolidinecarbothioamide,
16. N-(3-bromophenyl)-2-(2-chloro-5-ethoxy-4-pyridyl)-3-thiazolidinecarbothioamide,
17. N-(3-chloro-6-methylphenyl)-2-[4-(3-pyridyl)hexyl]-3-thiazolidinecarbothioamide,
18. N-(3-bromophenyl)-5-methyl-2-piperidinomethyl-3-thiazolidinecarbothioamide,
19. 2-[2-ethyl-3-(4-propylpiperidino)hexyl]-N-[6-propyl-3-(1,1,2,2-tetrafluoroethoxy)phenyl]-3-thiazolidinecarbothioamide,
20. N-(3-chlorophenyl)-5-ethyl-2-(3-ethyl-7,7-dimethyl-5-morpholinooctyl)-3-thiazolidinecarbothioamide,
21. N-(3-cyanophenyl)-2-[2-ethyl-4-(3-tetrahydrofuryl)hexyl]-3-thiazolidinecarbothioamide,
22. N-(3-bromophenyl)-2-methyl-4-isopropyl-3-thiazolidinecarbothioamide,
23. 2-hexyl-N-[3-(1,1,2,2-tetrafluoroethoxy)phenyl]-3-thiazolidinecarbothioamide,
24. 2-benzyl-2-ethyl-N-(3-fluorophenyl)-3-thiazolidinecarbothioamide,
25. N-(3-chlorophenyl)-6-isopropyl-6-methyl-2-neopentyltetrahydro-2H-1,3-thiazine-3-carbothioamide,
26. N-(3-cyano-5-isopropylphenyl)-2-(2,3,5-trimethyloctyl)tetrahydro-2H-1,3-thiazine-3-carbothioamide,
27. 4,6-dimethyl-6-ethyl-N-(3-iodophenyl)-2-pentadecyltetrahydro-2H-1,3-thiazine-3-carbothioamide,
28. 2-(2-ethylcyclobutyl)-N-(3-trifluoromethylphenyl)tetrahydro-2H-1,3-thiazine-3-carbothioamide,
29. 2-(3-isopropylcyclohexyl)-N-[3-(1,1,2,2-tetrafluoroethoxy)phenyl]tetrahydro-2H-1,3-thiazine-3-carbothioamide,
30. N-(3-bromo-4-chlorophenyl)-2-cyclododecyl-5,5-dimethyltetrahydro-2H-1,3-thiazine-3-carbothioamide,
31. N-(3-bromophenyl)-4-ethyl-2-(3-hexylthiophenyl)-6-methyltetrahydro-2H-1,3-thiazine-3-carbothioamide,
32. 2-(3-cyanophenyl)-N-(2-isopropyl)-3-chlorophenyl)tetrahydro-2H-1,3-thiazine-3-carbothioamide,
33. N-(3-fluorophenyl)-2-(2-methyl-4-trifluoromethylphenyl)-5-propyltetrahydro-2H-1,3-thiazine-3-carbothioamide,
34. 2-[3-(5-ethylcyclononyl)propyl]-N-(3-fluorophenyl)-4-methyltetrahydro-2H-1,3-thiazine-3-carbothioamide,
35. N-(2-ethyl-3-iodophenyl)-2-(2-phenyldecyl)tetrahydro-2H-1,3-thiazine-3-carbothioamide,
36. 5-ethyl-N-(3-trifluoromethylphenyl)-2-[2,2-dimethyl-3-(3-trifluoromethylphenyl)propyl]tetrahydro-2H-1,3-thiazine-3-carbothioamide,
37. 4-isopropyl-5-methyl-2-[1-phenyl-1-(3,5-dibromophenyl)ethyl]-N-[3-(1,1,2,2-tetrafluoroethoxy)phenyl]tetrahydro-2H-1,3-thiazine-3-carbothioamide,
38. 2-(4-ethyl-2-piperidino)-N-(3-fluorophenyl)tetrahydro-2H-1,3-thiazine-3-carbothioamide,
39. N-(3-chlorophenyl)-5-ethyl-2-[2-(3-isopropoxy-2-pyridyl)propyl]tetrahydro-2H-1,3-thiazine-3-carbothioamide,
40. N-(3-chlorophenyl)-4,5-dimethyl-2-(4-piperidinoundecyl)tetrahydro-2H-1,3-thiazine-3-carbothioamide,
41. N-(3-chlorophenyl)-2-[7-(4-isopropylpiperidino)nonyl]tetrahydro-2H-1,3-thiazine-3-carbothioamide,
42. N-(3-cyanophenyl)-2-[1-methyl-2-(3-isopropyl-2-pyrazinyl)ethyl]tetrahydro-2H-1,3-thiazine-3-carbothioamide,
43. N-(3-iodophenyl)-5-propyl-2-[13-(2-tetrahydrofuryl)tridecyl]tetrahydro-2H-1,3-thiazine-3-carbothioamide,
44. N-(3-cyanophenyl)-2-(3-methoxyphenyl)-6-methyltetrahydro-2H-1,3-thiazine-3-carbothioamide,
45. N-(3-cyanophenyl)-2-phenethyltetrahydro-2H-1,3-thiazine-3-carbothioamide,
46. N-(3-chlorophenyl)-2-[(2-ethyloctyl) (2-phenylpentyl)amino]tetrahydro-2H-1,3-thiazine-3-carbothioamide,
47. 2-(4-ethyldodecyl)-N-(2-ethyl-3-iodophenyl)benzothiazoline-3-carbothioamide,
48. N-(3-cyanophenyl)-7-methoxy-2-(5-propyl-2,6,9-trimethylundecyl)benzothiazoline-3-carbothioamide,
49. N-(3-bromo-6-methylphenyl)-2-(3-isopentylphenyl)benzothiazoline-3-carbothioamide,
50. N-(3-chloro-5-isopropylphenyl)-4-cyano-2-(2-fluorophenyl)benzothiazoline-3-carbothioamide,
51. 2-(2-isobutoxy-3-propylphenyl)-N-(3-trifluoromethylphenyl)benzothiazoline-3-carbothioamide,
52. 2-(3-chloro-5-ethylthiophenyl)-N-(3-iodophenyl)-5-trifluoromethylbenzothiazoline-3-carbothioamide,
53. N-(3-chlorophenyl)-2-(5,5-diphenylpentyl)benzothiazoline-3-carbothioamide,
54. 2-(4-pyridylmethyl)-N-(3-trifluoromethylphenyl)-benzothiazoline-3-carbothioamide,
55. 2-[10-(2-ethyl-3-pyridyl)decyl]-5-iodo-N-(3-trifluoromethylphenyl)benzothiazoline-3-carbothioamide,
56. N-(3-bromophenyl)-2-[2-(2,3-dimethylpiperidino)ethyl]benzothiazoline-3-carbothioamide,
57. N-(3-bromophenyl)-4-fluoro-2-(3-morpholinopropyl)benzothiazoline-3-carbothioamide,
58. N-(3-chlorophenyl)-4-methyl-2-[9-(2-pyrazinyl)nonyl]benzothiazoline-3-carbothioamide,
59. 2-dodecyl-5-isopropoxy-N-(3-trifluoromethylphenyl)benzothiazoline-3-carbothioamide,
60. N-(3-chlorophenyl)-2-(2,3-dibromophenyl)benzothiazoline-3-carbothioamide, and
61. N-(3-chlorophenyl)-2-[2-methyl-3-(4-ethylphenyl)propyl]benzothiazoline-3-carbothioamide.

The compounds of the present invention are prepared in accordance with methods well known to those having ordinary skill in the art. In general, the compounds can be prepared by reacting an appropriately-substituted thiazolidine, tetrahydro-2H-1,3-thiazine, or benzothiazoline with an equivalent amount of a suitably-substituted phenyl isothiocyanate. The reaction typically is carried out at ambient temperature for approximately 14 hours in a suitable solvent. If desired, shorter times will result by heating the reaction mixture at an elevated temperature, up to and including the reflux temperature of the reaction mixture. Furthermore, the reaction can be carried out in the presence of a catalytic amount of a tertiary amine or similar compound, such as triethylamine, triethylenediamine, or imidazole. Suitable solvents include, among others, benzene, toluene, the xylenes, chloroform, ethyl acetate, acetonitrile, and the like. Chloroform is the solvent of choice. The reaction mixture then is worked up in accordance with usual procedures. Typically, the solvent is removed under reduced pressure and the residue recrystallized from a suitable solvent or solvent combination. The most frequently used recrystallization solvents and solvent combinations are benzene, hexane, benzene/hexane, chloroform/hexane, ethyl acetate/hexane, ethanol, and aqueous ethanol.

The phenyl isothiocyanate starting materials are readily prepared by known methods from the corresponding amines (anilines). For example, the appropriately-substituted amine is reacted with N,N-dimethylthiocarbamoyl chloride in a suitable solvent, such as benzene, toluene, or a xylene. Typically, the reaction is carried out at reflux temperature for approximately 14 hours. The resulting phenyl isothiocyanate normally is isolated and purified by distillation. Alternatively, the appropriately-substituted aniline can be reacted with thiophosgene in chloroform in the presence of aqueous sodium carbonate at a temperature of 10°–15° C.

The thiazolidine, tetrahydro-2H-1,3-thiazine, and benzothiazoline starting materials also are prepared in accordance with known procedures. In general, the appropriate aldehyde or ketone is condensed with the corresponding mercaptoamine. Thus, the use of a mercaptoethylamine yields a thiazolidine, a mercaptopropylamine yields a tetrahydro-2H-1,3-thiazine, and a 2-aminothiophenol yields a benzothiazoline. When the mercaptoamine is employed as a salt a small amount of base is added to the reaction mixture and the product is washed with base.

The condensation reaction typically is carried out in either benzene or toluene and in the presence of about one-half equivalent of a base such as triethylamine. The water produced by the condensation reaction is removed by azeotropic condensation and is collected in a Dean-Stark trap. The reaction mixture then is washed with aqueous sodium or potassium hydroxide. The product then is isolated and purified in accordance with usual procedures.

With respect to the required aldehydes, ketones, and mercaptoamines, such compounds are either available commercially or readily prepared by known methods. For an excellent summary of typical preparative methods, see R. B. Wagner and H. D. Zook, "Synthetic Organic Chemistry," John Wiley and Sons, Inc., New York, 1965.

The examples which follow illustrate the preparations of representative compounds of the present invention. The first five examples illustrate the preparations of various intermediates. In most cases, the product was identified by elemental microanalysis and nuclear magnetic resonance analysis. Unless otherwise stated, all temperatures are given in degrees Celsius.

EXAMPLE 1. Preparation of 2-Decylthiazolidine.

A mixture of 34 g. of undecylaldehyde and 22.8 g. of 2-aminoethanethiol hydrochloride in about 400 ml. of toluene was heated at reflux overnight. The water of condensation was collected in a Dean-Stark trap. The reaction mixture then was washed with aqueous sodium hydroxide and dried over anhydrous magnesium sulfate. After filtering the reaction mixture, the toluene was distilled under reduced pressure. The residue then was vacuum distilled, b.p. 130°–8°/0.1 mm, giving 2-decylthiazolidine. The following elemental microanalysis was obtained:

Calculated for $C_{13}H_{27}NS$: C, 68.06; H, 11.86; N, 6.11. Found: C, 67.81; H, 11.66; N, 6.14.

EXAMPLE 2. Preparation of 2-(4-bromophenyl)thiazolidine.

The procedure of Example 1 was repeated, except that the reactants consisted of 18.5 g. of 4-bromobenzaldehyde and 27 g. of 2-aminoethanethiol hydrochloride, and the reaction mixture also contained 10 ml. of triethylamine. Since removal of solvent left a solid residue, the material was recrystallized from benzene/hexane to give 2-(4-bromophenyl)thiazolidine, m.p. 105°–7°. The following elemental analysis was obtained:

Calculated for $C_9H_{10}BrNS$: C, 44.27; H, 4.13; N, 5.74. Found: C, 44.50; H, 4.03; N, 5.74.

EXAMPLE 3. Preparation of 2-phenyltetrahydro-2H-1,3-thiazoline.

The procedure of Example 1 was repeated, except that the reactants consisted of 12.8 g. of benzaldehyde and 11 g. of 3-amino-1-propanethiol, the toluene was replaced with 200 ml. of benzene, and the reaction time was extended to about 65 hours. After the distillation of solvent, an oil remained to which was added 50 ml. of hexane, giving about 15 g. of white crystals of 2-phenyltetrahydro-2H-1,3-thiazoline, m.p. 64°–66° (reported, m.p. 65.6°–7°). The product was identified by nuclear magnetic resonance analysis only.

EXAMPLE 4. Preparation of 2-Ethylbenzothiazoline.

The procedure of Example 1 was repeated, except that the reactants consisted of 37.5 g. of 2-aminothiophenol and 17.5 g. of propionaldehyde. The residue which remained after the removal of solvent was distilled in vacuo, chromatographed on a silica gel column with toluene as eluant, and redistilled at 94°–104°/0.3 mm. to give 2-ethylbenzothiazoline. The following elemental micro-analysis was obtained:

Calculated for $C_9H_{11}NS$: C, 65.41; H, 6.71; N, 8.48. Found: C, 65.64; H, 6.66; N, 8.48.

EXAMPLE 5. Preparation of 3-Amino-1-propanethiol.

Hydrogen sulfide was bubbled into a solution, cooled in an ice-bath, of 27 g. of sodium methoxide in 200 ml. of methanol to a phenolphthalein end-point. To the reaction mixture then were added, still with ice-bath cooling, another 27 g. of sodium methoxide and 65 g. of 3-chloropropylamine hydrochloride. The reaction mixture was stirred for one hour at 0° and allowed to warm to ambient temperature. The reaction mixture was filtered to remove solids and the methanol was distilled from the filtrate. The residue then was distilled through a short-path distillation head. The distillate, 11 g., b.p. about 150°, solidified immediately. An additional 9.5 g. of product, 3-amino-1-propanethiol, was obtained by extracting the pot residue with methanol and filtering, followed by distillation of methanol-soluble material.

EXAMPLE 6. Preparation of N-(3-Chlorophenyl)-2-ethyl-3-thiazolidinecarbothioamide A mixture of 1.2 g. of 2-ethylthiazolidine and 1.7 g. of m-chlorophenyl isothiocyanate in about 100 ml. of chloroform was stirred at ambient temperature for about 64 hours. Hexane was added to the reaction mixture. The solid which precipitated was isolated by filtration and recrystallized from ethanol, giving 2.5 g. (87%) of N-(3-chlorophenyl)-2-ethyl-3-thiazolidinecarbothioamide, m.p. 116°–8°. The following elemental microanalysis was obtained:

Calculated for $C_{12}H_{15}ClN_2S_2$: C, 50.26; H, 5.24; N, 9.77. Found: C, 50.60; H, 5.14; N, 9.71.

Each of the following compounds was prepared in accordance with the general procedure of Example 6, using the appropriately-substituted thiazolidine and phenyl isothiocyanate. When available, the approximate reaction time, percent yield, melting point, recrystallization solvent, and elemental microanalysis are given for each compound.

EXAMPLE 7. N-(3-Bromophenyl)-2-ethyl-3-thiazolidinecarbothioamide 64 hours, 27%, 124°–5°, ethanol.

Calculated for $C_{12}H_{15}BrN_2S_2$: C, 43.51; H, 4.56; N, 8.46. Found: C, 43.31; H, 4.52; N, 8.54.

EXAMPLE 8. N-(3-Cyanophenyl)-2-ethyl-3-thiazolidinecarbothioamide 64 hours, 139°–41°, ethanol.

Calculated for $C_{13}H_{15}N_3S_2$: C, 56.29; H, 5.45; N, 15.15. Found: C, 55.97; H, 5.60; N, 15.08.

EXAMPLE 9. N-(3-Chlorophenyl)-2,2-dipropyl-3-thiazolidinecarbothioamide 16 hours, 55%, 106°–8°, aqueous ethanol and then benzene/hexane.

Calculated for $C_{16}H_{23}ClN_2S_2$: C, 56.04; H, 6.76; N, 8.17. Found: C, 56.25; H, 6.47; N, 8.10.

EXAMPLE 10. N-(3-Chlorophenyl)-2-nonyl-3-thiazolidinecarbothioamide 16 hours, 78%, 102°–4°, ethanol.

Calculated for $C_{19}H_{29}ClN_2S_2$: C, 59.27; H, 7.59; N, 7.28. Found: C, 59.21; H, 7.80; N, 7.23.

EXAMPLE 11. N-(3-Chlorophenyl)-2-decyl-3-thiazolidinecarbothioamide 64 hours, 78%, 94°–6°, ethanol.

Calculated for $C_{20}H_{31}ClN_2S_2$: C, 60.20; H, 7.83; N, 7.02. Found: C, 60.44; H, 7.68; N, 7.04.

EXAMPLE 12. N-(3-Bromophenyl)-2-decyl-3-thiazolidinecarbothioamide 16 hours, 34%, 94°–6°, ethanol. The reaction was carried out in benzene, rather than chloroform.

Calculated for $C_{20}H_{31}BrN_2S_2$: C, 54.16; H, 7.05; N, 6.32. Found: C, 54.14; H, 7.30; N, 6.33.

EXAMPLE 13. 2-Decyl-N-(3-iodophenyl)-3-thiazolidinecarbothioamide 16 hours, 53%, 95°–6°, ethanol.

Calculated for $C_{20}H_{31}IN_2S_2$: C, 48.98; H, 6.33; N, 5.71. Found: C, 47.79; H, 6.30; N, 5.72.

EXAMPLE 14. N-(3-Chlorophenyl)-2-phenyl-3-thiazolidinecarbothioamide 88 hours, 54%, 91°–3°, benzene/hexane.

Calculated for $C_{16}H_{15}ClN_2S_2$: C, 57.38; H, 4.51; N, 8.37. Found: C, 59.16; H, 4.50; N, 8.05 Found (w/o drying): C, 60.55; H, 4.64; N, 8.04 Found (block dried at 120): C, 51.80; H, 4.52; N, 8.07.

The sample is apparently undergoing decomposition.

EXAMPLE 15. N-(3-Fluorophenyl)-2-methyl-2-phenyl-3-thiazolidinecarbothioamide 88 hours, 144°–5°, ethanol.

Calculated for $C_{17}H_{17}FN_2S_2$: C, 61.42; H, 5.15; N, 8.43.

EXAMPLE 16. N-(3-Chlorophenyl)-2-methyl-2-phenyl-3-thiazolidinecarbothioamide 64 hours, 32%, 128°–30° C., ethanol.

Calculated for $C_{17}H_{17}ClN_2S_2$: C, 58.52; H, 4.91; N, 8.03. Found: C, 58.24; H, 5.05; N, 7.87.

EXAMPLE 17. 2-Methyl-2-phenyl-N-(3-trifluoromethylphenyl)-3-thiazolidinecarbothioamide 16 hours, 45%, 146°–8°, ethanol.

Calculated for $C_{18}H_{17}F_3N_2S_2$: C, 56.53; H, 4.48; N, 7.32. Found: C, 56.79; H, 4.85; N, 7.20.

EXAMPLE 18. N-(3-(Chlorophenyl)-2-ethyl-2-phenyl-3-thiazolidinecarbothioamide 16 hours, 6%, 134°–5°, ethanol.

Calculated for $C_{18}H_{19}ClN_2S_2$: C, 59.57; H, 5.28; N, 7.72. Found: C, 59.32; H, 5.28; N, 7.60.

EXAMPLE 19. N-(3-Chlorophenyl)-2-(o-tolyl)-3-thiazolidinecarbothioamide 16 hours, 160°–2°, ethanol.

Calculated for $C_{17}H_{17}ClN_2S_2$: C, 58.52; H, 4.91; N, 8.03. Found: C, 58.27; H, 4.91; N, 8.00.

EXAMPLE 20. 2-(4-Bromophenyl)-N-(3-chlorophenyl)-3-thiazolidinecarbothioamide 16 hours, 70%, 144°–5°, ethanol.

Calculated for $C_{16}H_{14}BrClN_2S_2$: C, 46.44; H, 3.41; N, 6.77. Found: C, 46.17; H, 3.42; N, 6.73.

EXAMPLE 21. N-(3-Chlorophenyl)-2-(2,4-dimethylphenyl)-3-thiazolidinecarbothioamide 64 hours, 83%, 148°–9°, ethanol.

Calculated for $C_{18}H_{19}ClN_2S_2$: C, 59.57; H, 5.28; N, 7.72. Found: C, 59.57; H, 5.09; N, 7.57.

EXAMPLE 22.
2-Benzyl-N-(3-chlorophenyl)-3-thiazolidinecarbothioamide 16 hours, 32%, 129°–31°, ethanol.
Calculated for $C_{17}H_{17}ClN_2S_2$: C, 58.52; H, 4.91; N, 8.03. Found: C, 58.78; H, 5.19; N, 7.85.

EXAMPLE 23.
N-(3-Chlorophenyl)-2-(3-pyridyl)-3-thiazolidinecarbothioamide 16 hours, 100%, 162°–5°, precipitated with hexane.
Calculated for $C_{15}H_{14}ClN_3S_2$: C, 53.65; H, 4.17; N, 12.56. Found: C, 53.47; H, 4.17; N, 12.48.

EXAMPLE 24. Preparation of N-(3-Chlorophenyl)-2-ethyltetrahydro-2H-1,3-thiazine-3-carbothioamide.

A mixture of 2.6 g. of 2-ethyltetrahydro-2H-1,3-thiazine, 3.4 g. of 3-chlorophenyl isothiocyanate, and 30 ml. of benzene was stirred, after an initial exotherm, at ambient temperature for about 64 hours. To the reaction mixture was added about 10 ml. of hexane, which caused white crystals to form. The mixture was cooled and filtered, and the solid was washed with hexane. The solid was recrystallized from about 500 ml. of 10:1 hexane:carbon tetrachloride to give N-(3-chlorophenyl)-2-ethyltetrahydro2H-1,3-thiazine-3-carbothioamide, m.p. 69°–73°. The following elemental microanalysis was obtained:
Calculated for $C_{13}H_{17}ClN_2S_2$: C, 51.90; H, 5.70; N, 9.31. Found: C, 51.61; H, 5.48; N, 9.19.

EXAMPLE 25. Preparation of N-(3-Bromophenyl)-2-ethyltetrahydro-2H-1,3-thiazine-3-carbothioamide The procedure of Example 24 was repeated, except that the reaction mixture consisted of 1.3 g. of 2-ethyltetrahydro-2H-1,3-thiazine, 2.1 g. of 3-bromophenyl isothiocyanate, 15 ml. of benzene, and 15 ml. of hexane. A white precipitate formed within minutes as reaction became exothermic. The solid was recrystallized from carbon tetrachloride which contained a little hexane, giving 1.7 g. (49%) of N-(3-bromophenyl)-2-ethyltetrahydro-2H-1,3-thiazine-3-carbothioamide, m.p. 77°–9°. The following elemental microanalysis was obtained:
Calculated for $C_{13}H_{17}BrN_2S_2$: C, 45.22; H, 4.96; N, 8.11; S, 18.57. Found: C, 43.82; H, 5.23; N, 8.16; S, 19.25.

EXAMPLE 26. Preparation of N-(3-Chlorophenyl)-2-decyltetrahydro-2H-1,3-thiazine-3-carbothioamide.

The procedure of Example 24 was repeated, except that the reactants consisted of 2.4 g. of 2-decyltetrahydro2H-1,3-thiazine and 1.7 g. of 3-chlorophenyl isothiocyanate. Solvent was distilled under reduced pressure. The residual oil was crystallized from hexane and recrystallized from ethanol to give 2.2 g. (53%) of N-(3-chlorophenyl)-2-decyltetrahydro-2H-1,3-thiazine-3-carbothioamide, m.p. 63°–5°. The following elemental microanalysis was obtained:
Calculated for $C_{21}H_{33}ClN_2S_2$: C, 61.06; H, 8.05; N, 6.78; S, 15.52. Found: C, 60.83; H, 7.85; N, 7.05; S, 15.59.

EXAMPLE 27. Preparation of N-(3-Bromophenyl)-2-decyltetrahydro-2H-1,3-thiazine-3-carbothioamide The procedure of Example 25 was repeated, except that the reactants consisted of 0.9 g. of 2-decyltetrahydro-2H-1,3-thiazine and 0.7 g. of 3-bromophenyl isothiocyanate. The product was recrystallized from ethanol to give N-(3-bromophenyl)-2-decyltetrahydro-2H-1,3-thiazine3-carbothioamide, m.p. 73°–4°. The following elemental microanalysis was obtained:
Calculated for $C_{21}H_{33}BrN_2S_2$: C, 55.13; H, 7.27; N, 6.12; S, 14.02. Found: C, 55.18; H, 7.03; N, 6.03; S, 13.83.

EXAMPLE 28. Preparation of N-(3-Chlorophenyl)-2-phenyltetrahydro-2H-1,3-thiazine-3-carbothioamide The reaction of 3.6 g. of 2-phenyltetrahydro2H-1,3-thiazine and 3.4 g. of 3-chlorophenyl isothiocyanate was carried ut as described in Example 24, except that the volume of benzene was increased to 40 ml. and the reaction time was reduced to about 16 hours. A first crop of product was obtained by filtering the reaction mixture and washing the isolated solid with benzene. A second crop was obtained by adding hexane to the filtrate from the first crop isolation. Both crops were recrystallized from ethanol, m.p. 132°–5° and 137°–8°, respectively, giving a total of 4.6 g. (66%) of N-(3-chlorophenyl)-2-phenyltetrahydro-2H-1,3-thiazine-3-carbothioamide. The following elemental microanalysis was obtained:
Calculated for $C_{17}H_{17}ClN_2S_2$: C, 58.52; H, 4.91; N, 8.03; S, 18.38. Found: C, 58.66; H, 5.17; N, 8.19; S, 18.08.

EXAMPLE 29. Preparation of N-(3-Bromophenyl)-2-phenyltetrahydro-2H-1,3-thiazine-3-carbothioamide.

The reaction of 2.4 g. of 2-phenyltetrahydro2H-1,3-thiazine with 2.9 g. of 3-bromophenyl isothiocyanate was carried out as described in Example 24, except that the reaction time was about 16 hours. The reaction mixture was worked up as described in Example 27, giving 4.3 g. (82%) of N-(3-bromophenyl)-2-phenyltetrahydro-2H-1,3-thiazine-3-carbothioamide, m.p. 135°–7°. The following elemental microanalysis was obtained:
Calculated for $C_{17}H_{17}BrN_2S_2$: C, 51.91; H, 4.36; N, 7.12; S, 16.30. Found: C, 51.87; H, 4.52; N, 6.96; S, 16.39.

EXAMPLE 30. Preparation of N-(3-Chlorophenyl)-2-(o-tolyl)tetrahydro-2H-1,3-thiazine-3-carbothioamide.

The procedure of Example 24 was repeated, except that the reactants consisted of 1.9 g. of 2-(o-tolyl)tetrahydro-2H-1,3-thiazine-3-carbothioamide and 1.7 g. of 3-chlorophenyl isothiocyanate. The product was recrystallized from ethanol to give 3.1 g. (86%) of N-(3-chlorophenyl)-2-(o-tolyl)tetrahydro-2H-1,3-thiazine-3-carbothioamide, m.p. 134°–6°. The following elemental microanalysis was obtained:
Calculated for $C_{18}H_{19}ClN_2S_2$: C, 59.57; H, 5.28; N, 7.72; S, 17.67. Found: C, 59.79; H, 5.57; N, 7.59; S, 17.49.

EXAMPLE 31. Preparation of N,2-Bis(3-chlorophenyl)tetrahydro-2H-1,3-thiazine-3-carbothioamide The procedure of Example 29 was repeated, except that the reactants consisted of 2.1 g. of 2-(3-chlorophenyl)tetrahydro-2H-1,3-thiazine and 1.7 g. of 3-chlorophenyl isothiocyanate, giving 3.3 g. (86%) of N,2-bis(3-chlorophenyl)tetrahydro-2H-1,3-thiazine-3-carbothioamide, m.p. 151°–3°. The following elemental microanalysis was obtained:

Calculated for $C_{17}H_{16}Cl_2N_2S_2$: C, 53.26; H, 4.21; N, 7.31; S, 16.73. Found: C, 53.10; H, 4.18; N, 7.45; S, 16.71.

EXAMPLE 32. Preparation of 2-(3-Chlorophenyl)-N-(3-trifluoromethylphenyl)tetrahydro-2H-1,3-thiazine-3-carbothioamide The procedure of Example 29 was repeated, except that the reactants consisted of 1.9 g. of 2-(3-chlorophenyl)tetrahydro-2H-1,3-thiazine and 1.8 g. of 3-trifluoromethylphenyl isothiocyanate, to give 2.7 g. (73%) of 2-(3-chlorophenyl)-N-(3-trifluoromethylphenyl)tetrahydro-2H-1,3-thiazine-3-carbothioamide, m.p. 143°–5°. The following elemental microanalysis was obtained:

Calculated for $C_{18}H_{16}ClF_3N_2S_2$: C, 51.86; H, 3.87; N, 6.72; S, 15.38. Found: C, 51.74; H, 4.01; N, 6.98; S, 15.22.

EXAMPLE 33. Preparation of 2-(4-Bromophenyl)-N-(3-chlorophenyl)tetrahydro-2H-1,3-thiazine-3-carbothioamide The procedure of Example 29 was repeated, except that the reactants consisted of 2.6 g. of 2-(4-bromophenyl)tetrahydro-2H-1,3-thiazine and 1.7 g. of 3-chlorophenyl isothiocyanate. The product was isolated by filtration, washed with benzene, and recrystallized from chloroform/benzene, giving 3.7 g. (86%) of 2-(4-bromophenyl)-N-(3-chlorophenyl)tetrahydro-2H-1,3-thiazine-3-carbothioamide, m.p. 144°–6°. The following elemental microanalysis was obtained:

Calculated for $C_{17}H_{16}BrClN_2S_2$: C, 47.73; H, 3.77; N, 6.55; S, 14.99. Found: C, 47.96; H, 3.93; N, 6.50; S, 14.64.

EXAMPLE 34. Preparation of N-(3-Chlorophenyl)-2-methylbenzothiazoline-3-carbothioamide.

A mixture of 1.5 g. of 2-methylbenzothiazoline, 1.7 g. of 3-chlorophenyl isothiocyanate, about 100 ml. of chloroform, and a catalytic amount of imidazole was heated at reflux for several hours. Since thin layer chromatographic analysis showed that reaction was not complete and that some 3-chlorophenyl isothiocyanate had been lost, an additional 1.2 g. of the isothiocyanate was added to the reaction mixture which then was heated at reflux for about 16 hours. The solvent was distilled under reduced pressure and the residue was recrystallized from ethanol to give N-(3-chlorophenyl)-2-methylbenzothiazoline-3-carbothioamide, m.p. 120°–2°. The following elemental microanalysis was obtained:

Calculated for $C_{15}H_{13}ClN_2S_2$: C, 56.15; H, 4.08; N, 8.73. Found: C, 55.91; H, 4.09; N, 8.44.

Each of the following compounds was prepared in accordance with the general procedure of Example 34, except that a second addition of isothiocyanate was not required. The approximate reaction time and catalyst, if present, are given for each compound. When available, the percent yield, melting point, recrystallization solvent, and elemental microanalysis also are given for each compound.

EXAMPLE 35. N-(3-Chlorophenyl)-2-ethylbenzothiazoline-3-carbothioamide 16 hours, 54%, 92°–5°, ethanol.
Calculated for $C_{16}H_{15}ClN_2S_2$: C, 57.40; H, 4.48; N, 8.37. Found: C, 57.80; H, 4.72; N, 8.50.

EXAMPLE 36. N-(3-Bromophenyl)-2-ethylbenzothiazoline-3-carbothioamide 16 hours, imidazole, 55%, 101°–3°, ethanol.
Calculated for $C_{16}H_{15}BrN_2S_2$: C, 50.66; H, 3.99; N, 7.38. Found: C, 50.55; H, 4.08; N, 7.28.

EXAMPLE 37. N-(3-Chlorophenyl)-2-isopropylbenzothiazoline-3-carbothioamide 64 hours, triethylenediamine, 69%, 117°–20°, ethanol.
Calculated for $C_{17}H_{17}ClN_2S_2$: C, 58.52; H, 4.91; N, 8.03. Found: C, 58.82; H, 4.84; N, 7.85.

EXAMPLE 38. N-(3-Chlorophenyl)-2-undecylbenzothiazoline-3-carbothioamide 16 hours, 33%, the product was chromatographed on silica gel with toluene as eluant.
Calculated for $C_{25}H_{33}ClN_2S_2$: C, 65.12; H, 7.21; N, 6.08. Found: C, 65.35; H, 7.17; N, 5.83.

EXAMPLE 39. N-(3-Chlorophenyl)-2-cyclohexylbenzothiazoline-3-carbothioamide 64 hours, imidazole, 134°–8°, ethanol.
Calculated for $C_{20}H_{21}ClN_2S_2$: C, 61.76; H, 5.44; N, 7.20. Found: C, 61.70; H, 5.48; N, 7.11.

EXAMPLE 40. 2-Benzyl-N-(3-chlorophenyl)benzothiazoline-3-carbothioamide 16 hours, imidazole, 48%, 144°–6°, aqueous ethanol.
Calculated for $C_{21}H_{17}ClN_2S_2$: C, 63.54; H, 4.32; N, 7.06. Found: C, 63.35; H, 4.49; N, 6.97.

The compounds of the present invention are useful for the control of insect pests. For example, the compounds are active against such insects as Mexican bean beetle, boll weevil, corn rootworm, cereal leaf beetle, borers, Colorado potato beetle, grain beetles, alfalfa weevil, carpet beetle, confused flour beetle, powder post beetle, wireworms, rice weevil, rose beetle, plum curculio, white grubs, melon aphid, rose aphid, white fly, grain aphid, corn leaf aphid, pea aphid, mealy-bugs, scales, leafhopper, citrus aphid, spotted alfalfa aphid, green peach aphid, bean aphid, milkweed bug, tarnished plant bug, box elder bug, bed bug, squash bug, chinch bug, housefly, yellow-fever mosquito, stable fly, horn fly, cabbage maggot, carrot rust fly, codling moth, cutworm, clothes moth, Indian meal moth, leafrollers, corn earworm, European corn borer, cabbage looper, cotton bollworm, bagworm, sod webworm, fall armyworm, German cockroach, and American cockroach.

Because the compounds of the present invention appear to function most effectively when ingested by the target insect, such compounds are particularly useful for the control of insect pests on plants, and especially for the control of Mexican bean beetles. In general, however, the compounds of the present invention can be applied to or incorporated into any food or water source for the target insect.

Thus, the present invention provides a method for reducing or eradicating a population of the insect species *Epilachna varivestis* which comprises administering to the insect by ingestion an insecticidally-effective amount of a compound of the present invention.

The term "insecticidally-effective amount" refers to an amount which results in the inactivation of the insect. Such inactivation can be lethal, either immediately or with delay, or it can be a sub-lethal inactivation in which the insect is rendered incapable of carrying out one or more of its normal life processes. Thus, the term "reducing or eradicating" means that the compound of the present invention can either kill all of the insect species to which the compound is administered, or that the administration of the compound reduces the population of such insect species. As is well known in the art, many known insecticides render the insect incapable of carrying out one or more of its normal life processes. Most often, the nervous system typically is seriously disturbed. However, the precise mechanism by which the compounds constituting the present invention operate is not yet known, and the insecticidal methods of the present invention are not limited by any mode of operation.

The utilization of an inactivating amount of one of the compounds of the present invention is critical to the present insecticidal method. The inactivating amount can sometimes be administered by employing the compound in unmodified form. However, for best results, it generally is necessary that the compound or compounds be employed in modified form; that is, as one component of a composition formulated to implement the insecticidal effects. Thus, for example, the active ingredient can be mixed with water or other liquid or liquids, preferably aided by the usage of a surface-active agent. The compounds also can be incorporated on finely-divided solid, which can be a substance having surface-active adsorption properties, to yield a wettable powder which subsequently can be dispersed in water or other liquid, or incorporated as part of a dust which can be applied directly. Other methods of formulation are known in the art and can be employed in implementing the present invention.

The exact concentration of one or more of the compounds of the present invention in a composition thereof with one or a plurality of adjuvants can vary; it is necessary only that one or more of the products be present in such amount as to make possible the application of an inactivating dosage to an insect. In many situations, a composition comprising about 0.001 percent by weight of the present active agent is effective for the administration of an inactivating amount thereof to insect pests. Compositions having a higher concentration of active agent, such as a concentration of from about 0.001 to about 0.5 percent can, of course, be employed. In still other operations, compositions containing from about 0.5 to about 98 percent by weight of one or more compounds are conveniently employed. Such compositions are adapted to be employed as treating compositions per se or as concentrates for subsequent dilution with additional adjuvant to produce ultimate treating compositions.

Liquid compositions containing the desired amount of active agent are prepared by dissolving the substance in an organic liquid or by dispersing the substance in water with or without the aid of a suitable surface-active dispersing agent such as an ionic or nonionic emulsifying agent. Such compositions also can contain modifying substances which serve to aid spreading and adhesion of the material on plant foliage. Suitable organic liquid carriers include the agricultural spray oils and the petroleum distillates such as diesel fuel, kerosene, fuel oil, naphthas, and Stoddard solvent. Among such liquids the petroleum distillates are generally preferred. The aqueous compositions can contain one or more water-immiscible solvents for the toxicant compound. In such aqueous compositions, the carrier comprises an aqueous emulsion, e.g., a mixture of water, emulsifying agent, and water-immiscible solvent. The choice of dispersing and emulsifying agent and the amount thereof employed is dictated by the nature of the composition and by the ability of the agent to facilitate the dispersing of the active agent in the carrier to produce the desired composition. Dispersing and emulsifying agents which can be employed in the compositions include the condensation products of alkylene oxides with phenols and organic acids, alkaryl sulfonates, polyoxyalkylene derivatives of sorbitan esters, complex ether alcohols, and the like. For a review of known surface-active agents which are suitably employed in implementing the present invention, attention is directed to U.S. Pat. No. 3,095,299, second column, lines 25–36, and references cited therein.

In the preparation of dust compositions, the active ingredient is intimately dispersed in and on a finely-divided solid such as clay, talc, chalk, gypsum, limestone, vermiculite fines, perlite, and the like. In one method of achieving such dispersion, the finely divided carrier is mechnically mixed or ground with the active agent.

Similarly, dust compositions containing the toxicant compounds can be prepared with various of solid carriers such as bentonite, fuller's earth, attapulgite, and other clays having surface-active adsorption properties. Depending upon the proportions of ingredients, these dust compositions can be employed as concentrates and subsequently diluted with additional adsorptive-type solid carriers or with chalk, talc, or gypsum, or the like to obtain the desired amount of active ingredient in a composition adapted to be employed in accordance with the present invention. Also, such dust compositions can be dispersed in water, with or without the aid of a dispersing agent, to form spray mixtures.

The compositions of the present invention also can be employed in granular formulations. These formulations are prepared in conventional manner, typically by dissolving the compound in a solvent with or without a surface-active agent and spraying or otherwise distributing the resulting solution onto pre-formed granules. Such granular formulations are capable of providing longer-lasting activity and may be preferred for crops such as corn where repeated application is not practical.

When operating in accordance with the present invention, one or more of the compounds or a composition containing one or more of the compounds is applied to a source of food or water for the pest to be controlled in any convenient manner, for example, by means of hand dusters or sprayers or by simple mixing with the food to be ingested by the pest. Application to the foliage of plants is conveniently carried out with power dusters, boom sprayers, and fog sprayers. In such foilar applications, the employed composition should not contain any appreciable amounts of any phytotoxic diluents. In large-scale operations, dust or low volume sprays can be applied from the air. The present invention also comprehends the employment of compositions comprising one or more compounds of the present invention, an adjuvant, and one or more other biologically-active materials, such as other insecticides, fungicides, miticides, bacteriocides, nematocides, and the like.

It is usual in describing foliar applications of plant protectants to measure the application rate by the concentration of dispersion in which it is applied. The application rate is measured in this way because it is customary to apply a sufficient amount of the dispersion to cover the foliage with a thin film. The amount of dispersion applied is thus dependent on the foliar area of the plant, and the quantity of plant-protecting compound is dependent upon its concentration in the dispersion.

Thus, in one embodiment, the insecticidal method is carried out by applying the compounds to the foliage of plants or other source of food for the insect, and applications are made in the same manner as already described. The insecticidal application rates are from about 100 ppm to about 2000 ppm. It is, of course, apparent that higher or lower concentrations can be employed, depending upon the insect species to be controlled, the plant or other food source to which application is to be made, and the potency or toxicity of the particular compound in the composition.

The activity of representative compounds of the present invention against Mexican bean beetle is illustrated by the following example.

EXAMPLE 41

The compounds to be tested were dissolved or suspended in 50:50 acetone-ethanol, and a blend of anionic and nonionic surfactants were added. The solution then was dispersed in water, so that the final dispersion contained about 20 percent of solvent and the concentration of test compound shown in the table below.

The test compound dispersions were sprayed on the foliage of young bean plants in an amount sufficient to wet the foliage completely. The dispersions then were allowed to dry, and individual leaves were removed from the plants. The petiole of each leaf was wrapped in water-soaked cotton and the leaf then was infested with second instar larvae of Mexican bean beetle. Five larvae were applied to each leaf, and two replicates were used for each compound concentration. Mortality was observed on the fourth and seventh days after treatment.

Untreated control insects were included with every group of test insects.

Insect mortality produced by the compound was rated on a scale where 0 represented no mortality, 1 represented less than 50 percent mortality, 2 represented 51–99 percent mortality, and 3 represented 100 percent mortality of insects. Results were averaged where a compound was tested repeatedly against the insect. Empty spaces in the table indicate that the compound was not tested at the indicated rate. The results produced by typical compounds of the invention are summarized in Table 1 which follows.

TABLE 1
ACTIVITY OF REPRESENTATIVE COMPOUNDS AGAINST MEXICAN BEAN BEETLE

| Compound of Example | ORIGINAL TEST | | | | RETEST | | | | |
|---|---|---|---|---|---|---|---|---|---|
| | 100 ppm. | | 100 ppm. | | 100 ppm. | 50 ppm. | 25 ppm. | 10 ppm. | 5 ppm. |
| | 4 days | 7 days | 4 days | 7 days | 7 days | 7 days | 7 days | 7 days | 7 days |
| 6 | 3 | 3 | 3 | 3 | 3 | 3 | 3 | 0 | |
| 7 | 3 | 3 | 3 | 3 | 3 | 3 | 3 | 1 | |
| 8 | 3 | 3 | 0 | 1 | 3 | 3 | 2 | 1 | |
| 9 | | | 3 | 3 | 3 | 3 | 3 | 1 | |
| 10 | 3 | 3 | 0 | 0 | | | | | |
| 11 | 3 | 3 | 0 | 0 | | | | | |
| 12 | | | 2 | 3 | 3 | 2 | 1 | 1 | |
| 13 | | | 1 | 3 | 2 | | | 1 | |
| 14 | 3 | 3 | 1 | 2 | | | | | |
| 15 | 0 | 0 | 1 | 1 | | | | | |
| 16 | 3 | 3 | 1 | 2 | | | | | |
| 17 | 0 | 3 | 0 | 1 | | | | | |
| 18 | 1 | 3 | 0 | 0 | | | | | |
| 19 | 2 | 3 | 0 | 0 | | | | | |
| 20 | 0 | 0 | 0 | 0 | | | | | |
| 21 | 2 | 3 | 0 | 1 | | | | | |
| 22 | | | 2 | 3 | 3 | 3 | 3 | | |
| 23 | 0 | 0 | 0 | 0 | | | | | |
| 24 | 3 | 3 | 3 | 3 | 3 | 2 | 2 | | |
| 25 | 3 | 3 | 3 | 3 | | | | | |
| 26 | 3 | 3 | 3 | 3 | 3 | | | 1 | |
| 27 | 3 | 3 | 3 | 3 | | | | | |
| 28 | 3 | 3 | 3 | 3 | 3 | 3 | 1 | | |
| 29 | 3 | 3 | 3 | 3 | 3 | 3 | 3 | 2 | |
| 30 | 3 | 3 | 3 | 3 | 3 | 3 | 3 | 1 | |
| 31 | 3 | 3 | 3 | 3 | 3 | | | 0 | |
| 32 | 3 | 3 | 3 | 3 | 3 | | | 1 | |
| 33 | 2 | 3 | 3 | 3 | 3 | 3 | 1 | | |
| 34 | 3 | 3 | 1 | 3 | 3 | 3 | 3 | 1 | |
| 35 | 3 | 3 | 3 | 3 | 3 | 3 | 3 | 2 | 0 |
| 36 | 3 | 3 | 2 | 3 | 3 | 3 | 3 | 0 | |
| 37 | 3 | 3 | 3 | 3 | 3 | 3 | 2 | 1 | |
| 38 | 0 | 3 | 0 | 1 | | | | | |
| 39 | 3 | 3 | 1 | 2 | | | | | |

TABLE 1-continued
ACTIVITY OF REPRESENTATIVE COMPOUNDS AGAINST MEXICAN BEAN BEETLE

| Compound of Example | ORIGINAL TEST | | | | RETEST | | | | |
|---|---|---|---|---|---|---|---|---|---|
| | 100 ppm. 4 days | 100 ppm. 7 days | 100 ppm. 4 days | 100 ppm. 7 days | 100 ppm. 7 days | 50 ppm. 7 days | 25 ppm. 7 days | 10 ppm. 7 days | 5 ppm. 7 days |
| 40 | 3 | 3 | 1 | 1 | | | | | |

What is claimed is:

1. A compound of the formula,

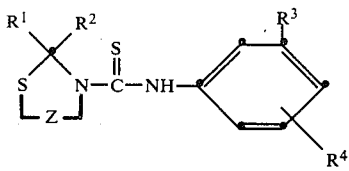

wherein
$R^1$ represents
- (A) $C_1$–$C_{18}$ alkyl;
- (B) $C_2$–$C_{18}$ alkenyl;
- (C) $C_4$–$C_{18}$ alkadienyl;
- (D) $C_3$–$C_{12}$ cycloalkyl, optionally substituted with either one or two $C_1$–$C_3$ alkyl groups;
- (E) $C_5$–$C_{12}$ cycloalkenyl, optionally substituted with either one or two $C_1$–$C_3$ alkyl groups;
- (F) $C_6$–$C_{12}$ cycloalkadienyl, optionally substituted with either one or two $C_1$–$C_3$ alkyl groups;
- (G) phenyl, optionally substituted with from one to three groups selected from the group consisting of
  - (1) $C_1$–$C_6$ alkyl,
  - (2) $C_1$–$C_6$ alkoxy,
  - (3) $C_1$–$C_6$ alkylthio,
  - (4) trifluoromethyl,
  - (5) halo, and
  - (6) cyano;
- (H) (cycloalkyl)alkyl, containing no more than about 18 carbon atoms, in which the cycloalkyl moiety is as defined hereinabove;
- (I) phenylalkyl, containing no more than about 18 carbon atoms, in which the phenyl moiety is as defined hereinabove;
- (J) diphenylalkyl, containing no more than about 18 carbon atoms, in which each phenyl moiety is as defined hereinabove;
- (K) pyridyl, optionally substituted with either one or two groups selected from the group consisting of
  - (1) $C_1$–$C_3$ alkyl,
  - (2) $C_1$–$C_3$ alkoxy, or
  - (3) halo;
- (L) piperidino attached at a position other than the nitrogen atom, optionally substituted with either one or two $C_1$–$C_3$ alkyl groups;
- (M) morpholino attached at a position other than the nitrogen atom;
- (N) pyrazinyl, optionally substituted with either one or two $C_1$–$C_3$ alkyl groups;
- (O) pyridylalkyl, containing no more than about 17 carbon atoms, in which the pyridyl moiety is as defined hereinabove;
- (P) piperidinoalkyl, containing no more than about 17 carbon atoms, in which the piperidino moiety is as defined hereinabove;
- (Q) morpholinoalkyl, containing no more than about 16 carbon atoms;
- (R) pyrazinylalkyl, containing no more than about 16 carbon atoms, in which the pyrazinyl moiety is as defined hereinabove; or
- (S) tetrahydrofurylalkyl, containing no more than about 17 carbon atoms;

$R^2$ represents hydrogen or $C_1$–$C_3$ alkyl;
$R^3$ represents
- (A) halo,
- (B) trifluoromethyl,
- (C) cyano, or
- (D) 1,1,2,2-tetrafluoroethoxy;

$R^4$ represents
- (A) hydrogen,
- (B) halo, or
- (C) $C_1$–$C_3$ alkyl, with the provisos that when $R^4$ is halo it can not be in the 2-position and when $R^4$ is $C_1$–$C_3$ alkyl it can not be in the 4-position;

Z represents

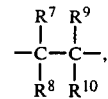 (A)

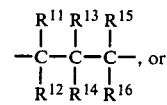 (B)

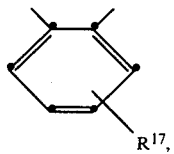 (C)

in which each of $R^7$–$R^{16}$, inclusive, independently is hydrogen or $C_1$–$C_3$ alkyl, with the proviso that the two groups attached to any given carbon atom in (A) or (B) together can not contain more than four carbon atoms; and $R^{17}$ represents
- (1) $C_1$–$C_3$ alkyl,
- (2) $C_1$–$C_3$ alkoxy,
- (3) $C_1$–$C_3$ alkylthio,
- (4) trifluoromethyl,
- (5) halo,
- (6) cyano, or
- (7) hydrogen;

with the proviso that when Z represents

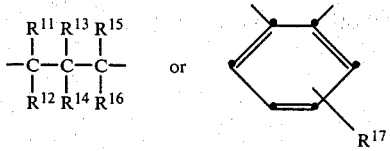

$R^2$ is hydrogen.

2. A compound of claim 1, wherein $R^1$ is alkyl; phenyl, optionally monosubstituted with halo or $C_1$–$C_3$ alkyl; or phenylalkyl in which the phenyl moiety is unsubstituted.

3. A compound of claim 1, wherein $R^3$ is halo or trifluoromethyl.

4. A compound of claim 1, wherein $R^4$ is hydrogen.

5. A compound of claim 1, wherein each of $R^7$–$R^{17}$, inclusive, is hydrogen.

6. A compound of claim 5, wherein Z is

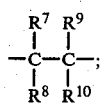

$R^1$ is alkyl; benzyl; or phenyl, optionally monosubstituted with bromo; $R^3$ is chloro or bromo; and $R^4$ is hydrogen.

7. A compound of claim 5, wherein Z is

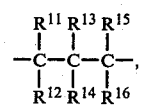

$R^1$ is alkyl; or phenyl, optionally monosubstituted with methyl, bromo, or chloro; $R^2$ is hydrogen; $R^3$ is bromo, chloro, or trifluoromethyl; and $R^4$ is hydrogen.

8. A compound of claim 5, wherein Z is

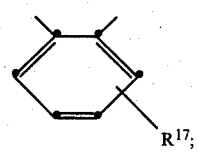

$R^1$ is $C_1$–$C_3$ alkyl; $R^2$ is hydrogen; $R^3$ is bromo or chloro; and $R^4$ is hydrogen.

9. The compound of claim 5, which compound is N-(3-bromophenyl)-2-ethyl-3-thiazolidinecarbothioamide.

10. The compound of claim 5, which compound is N-(3-chlorophenyl)-2-ethyl-3-thiazolidinecarbothioamide.

11. The compound of claim 5, which compound is N-(3-chlorophenyl)-2,2-dipropyl-3-thiazolidinecarbothioamide.

12. The compound of claim 5, which compound is N-(3-bromophenyl)-2-decyl-3-thiazolidinecarbothioamide.

13. The compound of claim 5, which compound is N-(3-chlorophenyl)-2-ethyl-2-phenyl-3-thiazolidinecarbothioamide.

14. The compound of claim 5, which compound is 2-(4-bromophenyl)-N-(3-chlorophenyl)-3-thiazolidinecarbothioamide.

15. The compound of claim 5, which compound is 2-benzyl-N-(3-chlorophenyl)-3-thiazolidinecarbothioamide.

16. The compound of claim 5, which compound is N-(3-bromophenyl)-2-ethyltetrahydro-2H-1,3-thiazine-3-carbothioamide.

17. The compound of claim 5, which compound is N-(3-chlorophenyl)-2-ethyltetrahydro-2H-1,3-thiazine-3-carbothioamide.

18. The compound of claim 5, which compound is N-(3-bromophenyl)-2-decyltetrahydro-2H-1,3-thiazine-3-carbothioamide.

19. The compound of claim 5, which compound is N-(3-chlorophenyl)-2-decyltetrahydro-2H-1,3-thiazine-3-carbothioamide.

20. The compound of claim 5, which compound is N-(3-bromophenyl)-2-phenyltetrahydro-2H-1,3-thiazine-3-carbothioamide.

21. The compound of claim 5, which compound is N-(3-chlorophenyl)-2-phenyltetrahydro-2H-1,3-thiazine-3-carbothioamide.

22. The compound of claim 5, which compound is N-(3-chlorophenyl)-2-(2-methylphenyl)tetrahydro-2H-1,3-thiazine-3-carbothioamide.

23. The compound of claim 5, which compound is 2-(4-bromophenyl)-N-(3-chlorophenyl)tetrahydro-2H-1,3-thiazine-3-carbothioamide.

24. The compound of claim 5, which compound is 2,N-bis(3-chlorophenyl)tetrahydro-2H-1,3-thiazine-3-carbothioamide.

25. The compound of claim 5, which compound is 2-(3-chlorophenyl)-N-(3-trifluoromethylphenyl)tetrahydro-2H-1,3-thiazine-3-carbothioamide.

26. The compound of claim 5, which compound is N-(3-chlorophenyl)-2-methylbenzothiazoline-3-carbothioamide.

27. The compound of claim 5, which compound is N-(3-bromophenyl)-2-ethylbenzothiazoline-3-carbothioamide.

28. The compound of claim 5, which compound is N-(3-chlorophenyl)-2-ethylbenzothiazoline-3-carbothioamide.

29. The compound of claim 5, which compound is N-(3-chlorophenyl)-2-isopropylbenzothiazoline-3-carbothioamide.

30. A method for reducing or eradicating a population of the insect species *Epilachna varivestis* which comprises administering to the insect by ingestion an insecticidally-effective amount of a compound of claim 1.

31. A method of claim 30, wherein $R^1$ is alkyl; phenyl, optionally monosubstituted with halo or $C_1$–$C_3$ alkyl; or phenylalkyl in which the phenyl moiety is unsubstituted.

32. A method of claim 30, wherein $R^3$ is halo or trifluoromethyl.

33. A method of claim 30, wherein $R^4$ is hydrogen.

34. A method of claim 30, wherein each of $R^7$–$R^{17}$, inclusive, is hydrogen.

35. A method of claim 34, wherein Z is

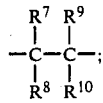

$R^1$ is alkyl; benzyl; or phenyl, optionally monosubstituted with bromo; $R^3$ is chloro or bromo; and $R^4$ is hydrogen.

36. A method of claim 34, wherein Z is

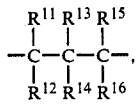

$R^1$ is alkyl; or phenyl, optionally monosubstituted with methyl, bromo, or chloro; $R^2$ is hydrogen; $R^3$ is bromo, chloro, or trifluoromethyl; and $R^4$ is hydrogen.

37. A method of claim 34, wherein Z is

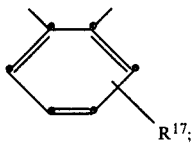

$R^1$ is $C_1$–$C_3$ alkyl; $R^2$ is hydrogen; $R^3$ is bromo or chloro; and $R^4$ is hydrogen.

38. The method of claim 34, in which the compound is N-(3-bromophenyl)-2-ethyl-3-thiazolidinecarbothioamide.

39. The method of claim 34, in which the compound is N-(3-chlorophenyl)-2-ethyl-3-thiazolidinecarbothioamide.

40. The method of claim 34, in which the compound is N-(3-chlorophenyl)-2,2-dipropyl-3-thiazolidinecarbothioamide.

41. The method of claim 34, in which the compound is N-(3-bromophenyl)-2-decyl-3-thiazolidinecarbothioamide.

42. The method of claim 34, in which the compound is N-(3-chlorophenyl)-2-ethyl-2-phenyl-3-thiazolidinecarbothioamide.

43. The method of claim 34, in which the compound is 2-(4-bromophenyl)-N-(3-chlorophenyl)-3-thiazolidinecarbothioamide.

44. The method of claim 34, in which the compound is 2-benzyl-N-(3-chlorophenyl)-3-thiazolidinecarbothioamide.

45. The method of claim 34, in which the compound is N-(3-bromophenyl)-2-ethyltetrahydro-2H-1,3-thiazine-3-carbothioamide.

46. The method of claim 34, in which the compound is N-(3-chlorophenyl)-2-ethyltetrahydro-2H-1,3-thiazine-3-carbothioamide.

47. The method of claim 34, in which the compound is N-(3-bromophenyl)-2-decyltetrahydro-2H-1,3-thiazine-3-carbothioamide.

48. The method of claim 34, in which the compound is N-(3-chlorophenyl)-2-decyltetrahydro-2H-1,3-thiazine-3-carbothioamide.

49. The method of claim 34, in which the compound is N-(3-bromophenyl)-2-phenyltetrahydro-2H-1,3-thiazine-3-carbothioamide.

50. The method of claim 34, in which the compound is N-(3-chlorophenyl)-2-phenyltetrahydro-2H-1,3-thiazine-3-carbothioamide.

51. The method of claim 34, in which the compound is N-(3-chlorophenyl)-2-(2-methylphenyl)tetrahydro-2H-1,3-thiazine-3-carbothioamide.

52. The method of claim 34, in which the compound is 2-(4-bromophenyl)-N-(3-chlorophenyl)tetrahydro-2H-1,3-thiazine-3-carbothioamide.

53. The method of claim 34, in which the compound is 2,N-bis(3-chlorophenyl)tetrahydro-2H-1,3-thiazine-3-carbothioamide.

54. The method of claim 34, in which the compound is 2-(3-chlorophenyl)-N-(3-trifluoromethylphenyl)tetrahydro-2H-1,3-thiazine-3-carbothioamide.

55. The method of claim 34, in which the compound is N-(3-chlorophenyl)-2-methylbenzothiazoline-3-carbothioamide.

56. The method of claim 34, in which the compound is N-(3-bromophenyl)-2-ethylbenzothiazoline-3-carbothioamide.

57. The method of claim 34, in which the compound is N-(3-chlorophenyl)-2-ethylbenzothiazoline-3-carbothioamide.

58. The method of claim 34, in which the compound is N-(3-chlorophenyl)-2-isopropylbenzothiazoline-3-carbothioamide.

59. An insecticidal composition which comprises an insecticidally-effective amount of a compound of claim 1 and an agriculturally-acceptable carrier.

60. A composition of claim 59, wherein $R^1$ is alkyl; phenyl, optionally monosubstituted with halo or $C_1$–$C_3$ alkyl; or phenylalkyl in which the phenyl moiety is unsubstituted.

61. A composition of claim 59, wherein $R^3$ is halo or trifluoromethyl.

62. A composition of claim 59, wherein $R^4$ is hydrogen.

63. A composition of claim 59, wherein each of $R^7$–$R^{17}$, inclusive, is hydrogen.

64. A composition of claim 63, wherein Z is

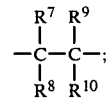

$R^1$ is alkyl; benzyl; or phenyl, optionally monosubstituted with bromo; $R^3$ is chloro or bromo; and $R^4$ is hydrogen.

65. A composition of claim 63, wherein Z is

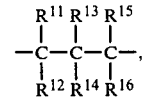

$R^1$ is alkyl; or phenyl, optionally monosubstituted with methyl, bromo, or chloro; $R^2$ is hydrogen; $R^3$ is bromo, chloro, or trifluoromethyl; and $R^4$ is hydrogen.

66. A composition of claim 63, wherein Z is

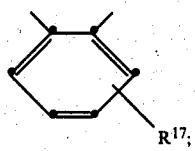

$R^1$ is $C_1$–$C_3$ alkyl; $R^2$ is hydrogen; $R^3$ is bromo or chloro; and $R^4$ is hydrogen.

67. The composition of claim 63, in which the compound is N-(3-bromophenyl)-2-ethyl-3-thiazolidinecarbothioamide.

68. The composition of claim 63, in which the compound is N-(3-chlorophenyl)-2-ethyl-3-thiazolidinecarbothioamide.

69. The composition of claim 63, in which the compound is N-(3-chlorophenyl)-2,2-dipropyl-3-thiazolidinecarbothioamide.

70. The composition of claim 63, in which the compound is N-(3-bromophenyl)-2-decyl-3-thiazolidinecarbothioamide.

71. The composition of claim 63, in which the compound is N-(3-chlorophenyl)-2-ethyl-2-phenyl-3-thiazolidinecarbothioamide.

72. The composition of claim 63, in which the compound is 2-(4-bromophenyl)-N-(3-chlorophenyl)-3-thiazolidinecarbothioamide.

73. The composition of claim 63, in which the compound is 2-benzyl-N-(3-chlorophenyl)-3-thiazolidinecarbothioamide.

74. The composition of claim 63, in which the compound is N-(3-bromophenyl)-2-ethyltetrahydro-2H-1,3-thiazine-3-carbothioamide.

75. The composition of claim 63, in which the compound is N-(3-chlorophenyl)-2-ethyltetrahydro-2H-1,3-thiazine-3-carbothioamide.

76. The composition of claim 63, in which the compound is N-(3-bromophenyl)-2-decyltetrahydro-2H-1,3-thiazine-3-carbothioamide.

77. The composition of claim 63, in which the compound is N-(3-chlorophenyl)-2-decyltetrahydro-2H-1,3-thiazine-3-carbothioamide.

78. The composition of claim 63, in which the compound is N-(3-bromophenyl)-2-phenyltetrahydro-2H-1,3-thiazine-3-carbothioamide.

79. The composition of claim 63, in which the compound is N-(3-chlorophenyl)-2-phenyltetrahydro-2H-1,3-thiazine-3-carbothioamide.

80. The composition of claim 63, in which the compound is N-(3-chlorophenyl)-2-(2-methylphenyl)tetrahydro-2H-1,3-thiazine-3-carbothioamide.

81. The composition of claim 63, in which the compound is 2-(4-bromophenyl)-N-(3-chlorophenyl)tetrahydro-2H-1,3-thiazine-3-carbothioamide.

82. The composition of claim 63, in which the compound is 2,N-bis(3-chlorophenyl)tetrahydro-2H-1,3-thiazine-3-carbothioamide.

83. The composition of claim 63, in which the compound is 2-(3-chlorophenyl)-N-(3-trifluoromethylphenyl)tetrahydro-2H-1,3-thiazine-3-carbothioamide.

84. The composition of claim 63, in which the compound is N-(3-chlorophenyl)-2-methylbenzothiazoline-3-carbothioamide.

85. The composition of claim 63, in which the compound is N-(3-bromophenyl)-2-ethylbenzothiazoline-3-carbothioamide.

86. The composition of claim 63, in which the compound is N-(3-chlorophenyl)-2-ethylbenzothiazoline-3-carbothioamide.

87. The composition of claim 63, in which the compound is N-(3-chlorophenyl)-2-isopropylbenzothiazoline-3-carbothioamide.

* * * * *

UNITED STATES PATENT AND TRADEMARK OFFICE
CERTIFICATE OF CORRECTION

PATENT NO. : 4,289,766
DATED : September 15, 1981
INVENTOR(S) : Terry W. Balko and Ronald E. Hackler It is certified that error appears in the above-identified patent and that said Letters Patent are hereby corrected as shown below:

Column 18, line 6, "C, 47.79; H, 6.30; N, 5.72" should read --C, 47.79; H, 6.30; N, 5.72; C, 48.91; H, 6.10; N, 5.49--.

Column 18, Line 24, "8.43" should read --8.43. Found C, 61.30; H, 5.29; N, 8.22--.

Column 26 & 27 Table 1, heading <u>Original Test</u>, left column "100 ppm." should read --1000 ppm.--.

Signed and Sealed this

First Day of June 1982

[SEAL]

Attest:

GERALD J. MOSSINGHOFF

Attesting Officer

Commissioner of Patents and Trademarks